United States Patent [19]
Beggs et al.

[11] Patent Number: 5,490,988
[45] Date of Patent: Feb. 13, 1996

[54] DELIVERY OF THERAPEUTIC AGENTS TO A TARGET SITE

[75] Inventors: Thomas S. Beggs, Bedford; Paul J. Davis, Bedfordshire; Martine E. Verhoeyen, Northants, all of England

[73] Assignee: Chesebrough-Pond's USA Co., Division of Conopco, Inc., Greenwich, Conn.

[21] Appl. No.: 335,925

[22] Filed: Nov. 8, 1994

Related U.S. Application Data

[63] Continuation of Ser. No. 22,781, Feb. 23, 1993, abandoned, which is a continuation of Ser. No. 771,670, Oct. 4, 1991, abandoned.

[30] Foreign Application Priority Data

Oct. 5, 1990 [GB] United Kingdom .................. 90211671

[51] Int. Cl.⁶ .............................. A61K 7/16; A61K 9/20; A61K 39/00
[52] U.S. Cl. ......................... 424/464; 424/49; 424/134.1; 424/150.1; 424/164.1; 424/165.1
[58] Field of Search ................................ 424/464, 49, 50, 424/440, 441, 85.8, 85.91; 514/21; 530/810–816

[56] References Cited

U.S. PATENT DOCUMENTS

| | | | |
|---|---|---|---|
| 4,657,853 | 4/1987 | Freytag | 435/7 |
| 4,725,428 | 2/1988 | Miyahara et al. | 424/50 |
| 4,808,700 | 2/1989 | Anderson | 530/403 |
| 4,943,525 | 7/1990 | Dawson | 435/7 |
| 4,975,278 | 12/1990 | Senter | 424/94.3 |

FOREIGN PATENT DOCUMENTS

| | | |
|---|---|---|
| 0175560 | 3/1986 | European Pat. Off. . |
| 0315364 | 5/1989 | European Pat. Off. . |
| 0368684 | 5/1990 | European Pat. Off. . |
| 0450800 | 10/1991 | European Pat. Off. . |
| 86/01533 | 3/1986 | WIPO . |
| 8705031 | 8/1987 | WIPO . |
| 88/01178 | 2/1988 | WIPO . |
| 89/09825 | 10/1989 | WIPO . |
| 89/11866 | 12/1989 | WIPO . |
| 90/03185 | 4/1990 | WIPO . |
| 90/09803 | 9/1990 | WIPO . |
| 91/00112 | 1/1991 | WIPO . |
| 91/00108 | 1/1991 | WIPO . |
| 9105856 | 5/1991 | WIPO . |
| 91/08482 | 6/1991 | WIPO . |

OTHER PUBLICATIONS

Knowles et al, J. Clinical Investigation 52 1443 (1973).
Saiki et al, Science 230 1350 (1985).
Oranei et al, Proc. Natl. Acad. Sci. USA 86 3833 (1989).
John Hodgson in Biotechnology, vol. 9, p. 422 (May 1991).
European Search Report.

*Primary Examiner*—Gollamudi S. Kishore
*Attorney, Agent, or Firm*—Rimma Mitelman

[57] ABSTRACT

An antibody fragment able to bind to a target site is prolonged by an additional peptide. The Therapeutic agent is bound to this peptide or means are provided to bring about such binding. The antibody fragment and possibly also the therapeutic agent are included in a product so that binding to the target site delivers the therapeutic agent to the vicinity. The product may for example be for dental care, such as a toothpaste or mouthwash and the antibody fragment may then bind to a component of dental plaque.

10 Claims, 1 Drawing Sheet

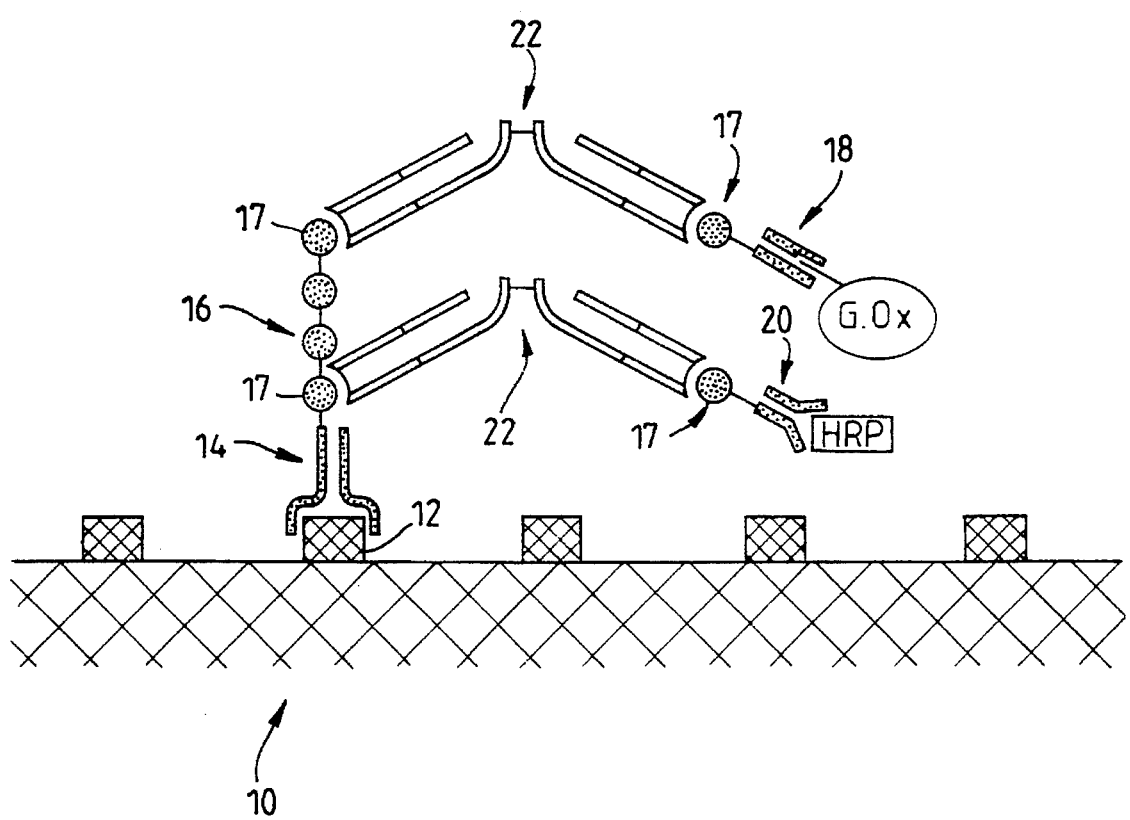

DELIVERY OF THERAPEUTIC AGENTS TO A TARGET SITE

This is a continuation application of Ser. No. 08/022,781, filed Feb. 23, 1993, now abandoned, which is a continuation of Ser. No. 07/771,670, filed Oct. 4, 1991, now abandoned.

FIELD AND BACKGROUND OF THE INVENTION

This invention relates to the delivery of therapeutic agents to target sites, with provision for binding to the target sites.

The use of an antibody/antigen binding as a means to attach a therapeutic agent to a target site has already been proposed, for example with glucose oxidase as the therapeutic agent. This enzyme catalyses the oxidation of glucose to gluconic acid by molecular oxygen, producing hydrogen peroxide in the process. Hydrogen peroxide is rapidly decomposed in vivo, but if it can be brought close to target cells it does exhibit toxicity to those cells.

As an example of such a proposal, using whole antibodies, Knowles et al J. Clinical Investigation 52 1443 (1973) have described the use of glucose oxidase chemically conjugated to antibodies capable of binding to target cells, thereby targeting the cell killing activity against those cells which it is desired to eliminate selectively. Cell killing, however, was only achieved if other (non-targeted) enzymes were present in the surrounding medium to generate even more toxic species.

WO 89/11866 (Rama Biolink) discloses antibiotic conjugated to anti *S. mutans* antibodies obtained by immunisation of hens.

The use of fragments of antibodies, rather than whole antibodies, to effect immunological binding, has been proposed in various documents including EP-A-175560 and EP-A-315364 which mention chemical conjugation to antibody fragments.

Techniques for expressing variable domains in bacteria, and hence producing Fv fragments of antibodies, are described by Saikl et al Science, 230 1350 (1985) and by Oranei et al Procnatl Acad Sci U.S.A. 88 3833 (1989). Production of antibody fragments is also discussed in EP-A-368684 (M.R.C.). This mentions the possibility of producing antibody fragment joined through a linking peptide to a protein having a required function, so that the peptide chain of the antibody fragment, the linking peptide and the functional protein are all expressed as a single fusion protein. Producing such a single protein has the difficulty that the yield of expressed protein may be low.

Expression of antibody fragments with the peptide chain prolonged and terminated by an additional peptide, to act as a linker, is described in our WO 91/08492 published 13 Jun. 1991.

SUMMARY OF THE INVENTION

Broadly the present invention makes use of an antibody fragment for binding to a target site, and provides for a therapeutic agent to be connected onto the antibody fragment through an additional peptide appended to the antibody fragment, thereby to attach the agent to the target site.

One aspect of the present invention provides a product comprising one or more vehicles which contain, in the same vehicle or distributed among separate vehicles, an antibody fragment which is able to bind to a target site and which has an additional peptide appended to it, and means for binding a therapeutic agent to the additional peptide.

The product may contain the therapeutic agent although not necessarily in the same vehicle as the antibody fragment.

The invention also includes a method of delivering a therapeutic agent to a target site comprising exposing the target site to a said antibody fragment with an additional peptide appended and means for binding a therapeutic agent to the additional peptide.

In a further aspect the invention provides the use of a said antibody fragment with an additional peptide appended, to prepare a product for topical application in order to attach a therapeutic agent to a target site.

DETAILED DISCUSSION

The antibody fragment is, as mentioned, able to bind to a target site through antibody-antigen binding. The additional peptide, being present for another purpose, will in general not contribute to these binding properties of the antibody fragment.

Attachment of the additional protein to the antibody fragment is through a peptide bond to an end of the antibody fragment peptide chain. In consequence this peptide chain of the antibody fragment is prolonged by the peptide which then forms a terminal portion of the resulting composite protein. One terminal amino acid of the protein will be an amino acid of the antibody fragment. The other will be an amino acid of the additional peptide.

The antibody fragment may be an Fv fragment of an antibody to the desired target. Such a fragment contains only the variable domains of light and heavy chains of an antibody. The fragment could possibly be an $F(ab)_2$ fragment which would provide two combining sites. It might alternatively be as little as a single variable domain of one peptide chain of an antibody.

Production of an antibody fragment which has an additional peptide chain appended to it can be by expression in bacteria. Bacteria can be made to express a variable domain with an extra peptide chain already attached to the C terminus of the domain: all that is necessary is to synthesise the appropriate short nucleic acid sequence and add this to the nucleic acid which codes for the variable domain. This can be done by standard techniques.

The production of antibody fragments with attached peptide is described in detail in our WO 91/08492 referred to above.

The additional peptide is valuable as a "handle" for the attachment of the therapeutic agent. Direct attachment to the antibody fragment runs the risk that the attached therapeutic agent hinders or blocks the antigen-antibody binding function. Attachment to the additional peptide reduces the likelihood of this. Attachment to the additional peptide will generally be to a part of the peptide between the antibody fragment and the terminus of the chain.

Means for binding a therapeutic agent may simply be covalent bonding between the additional peptide and the therapeutic agent.

Conjugation of molecules by chemical reactions which join them through covalent bonds is well known, and standard methods are available. WO 91/08492 referred to above describes covalent bonding to an additional peptide appended to an antibody fragment. As is recommended in that disclosure, the additional peptide may be designed to facilitate the attachment of other molecules through covalent bonding. In particular the additional peptide may include a lysine residue for the purpose.

When the therapeutic agent is bound through chemical bonds, the product will contain the antibody fragment with the additional peptide, and also the therapeutic agent bound to the additional peptide.

In another form of this invention the means for binding the therapeutic agent to the first mentioned antibody fragment comprises at least one additional antibody fragment. One possibility here is for the therapeutic agent to be covalently conjugated to a second antibody fragment which is able to bind by antibody antigen binding to the first mentioned antibody fragment.

An alternative, preferred possibility is that there is a second antibody fragment able to bind to the therapeutic agent by antibody-antigen binding, and there are means to couple the two antibody fragments to each other. Such means could be a F(ab)$_2$ fragment (bivalent) able to bind to the two antibody fragments, especially to antigenic peptides appended to the first and second antibody fragments.

This preferred possibility has the advantage that the entire connection between the therapeutic agent and the target site can assemble itself together, which can avoid subjecting delicate materials to chemical reactions required to form covalent bonds.

In a significant development, which is a further possibility within this invention, two co-operating therapeutic agents are utilised and there are means to bind both of these to aforesaid antibody fragments able to bind to the target site. This can then lead to both of the therapeutic agents being held in proximity to each other— promoting their co-operation—and to the target site, while avoiding steric hindrance and interference from relatively bulky whole antibodies which might otherwise do the same job. This encourages spontaneous self-assembly of the whole complex in its optimum configuration.

Preferably, means for attaching each therapeutic agent to the first aforementioned antibody fragment comprises at least one additional antibody fragment. Particularly preferred is that there are respective antibody fragments able to bind to each of the therapeutic agents, and means to couple these antibody fragments to the first mentioned antibody fragment which binds to the target site.

The invention could be used to deliver to a variety of different target sites.

The invention may in particular be used for delivery to target sites which are accessible by topical application, as contrasted with requiring the antibody fragment and any other materials to enter the blood stream. Thus, the invention may be used for delivery to target sites which are accessible by topical application to the body surface, target sites in the mouth, and target sites in material temporarily removed from the body.

One significant application is delivery of cytotoxic agents to species of the supragingival oral microflora. The oral microflora is a complex ecosystem which contains a wide variety of microbial species. One of these species may be selected as the target site. However, the likely effect of targeting to one species will be to attack both that species and other species which occur in close proximity to it. Thus, by delivering to one species which occurs in dental plaque, cytotoxic agents will be delivered to the plaque and will be likely to act against all the species which occur together in the plaque, including those responsible for plaque formation.

Extra-cellular dextran produced by such organisms could itself be used as the target site in which case the first antibody fragment is a fragment of an antibody to dextran.

One possible target species is *Streptococcus mutans*. This has been identified as an important contributor to dental plaque, and has been shown to be capable of inducing clinical caries lesions in germ-free animals when established as a mono-infection. *S. mutans* has the ability to utilise dietary carbohydrate for the synthesis of an insoluble polysaccharide matrix, facilitating attachment to, and colonisation of, hard surfaces, as well as production of acids capable of the dissolution of enamel. These characteristics have been identified as important virulence determinants. Although other species and genera have also proved capable of both acid and plaque production, or even of caries initiation in the germ-free animal, *S. mutans* is widely recognised as at least one significant cause of tooth decay because of the scale of its acid and polysaccharide production.

Other species which may be selected as the target species are *S. sanguis, A. viscosus* and *A. naeslundii*. These are all present in dental plaque as a substantial proportion of the species normally found in dental plaque. Because of frequent occurrence these three may be preferred target species.

As will be apparent, it is envisaged that the first antibody fragment may be suitable to bind to an antigenic component of dental plaque. In a particularly envisaged application of this invention, the first antibody fragment is a fragment of an antibody to *S. mutans, S. sanguis, A. viscosus* or *A. naeslundii* and the therapeutic agent is the enzyme glucose oxidase.

Another application is to attack species of the subgingival microflora responsible for periodontal disease. The target species could well be *Bacterioides gingivalis*.

For these oral applications (dental care) it would be appropriate for the vehicle(s) in the product to be suitable for topical application in the mouth.

Another possible application is to deliver therapeutic agents to attack human tumour cells, notably in bone marrow which has been removed temporarily from the body of a patient undergoing radiotherapy.

For all applications the therapeutic agent will be formed separately from the antibody with appended peptide. Various materials are contemplated as the therapeutic agents which may be delivered in accordance with this invention. One important possibility is an enzyme able to generate a cytotoxic product: glucose oxidase has been mentioned above. Galactose oxidase is another. If the target site is in the mouth, the substrate for this enzyme could be the galactose which occurs naturally in yoghurt. Further possibilities are xanthine oxidase which produces superoxide and NADP oxidase which also does so.

Other enzymes which might be delivered to a target site are lysozyme, to attack the cell wall of a gram negative bacterium or proteases to attack extracellular enzymes such as those which help to form dental plaque.

Another category of materials which could be delivered by means of the invention are enzyme inhibitors, which could act to inhibit extracellular enzymes of a target organism.

Further possibilities are oxygen generators or acid producers which could act to modify the environment in the vicinity of a target site. A particular possibility arises if the target site is in the periodontal pocket. Generating oxygen or reducing pH in this cavity would give conditions less favourable for the anaerobic organisms which can invade this pocket.

Yet another possibility is to deliver a material able to remove a limiting nutrient. More specifically, aerobactin, enterochelin or porphyrin could be delivered to a target in the periodontal pocket. They would complex with iron and reduce the concentration of iron available to bacterial invaders of this pocket. These materials could be used in their simplest state as the therapeutic agent. However, they could be used in glycosylated form in which the glyosyl chains would be antigenic, allowing the possibility of binding by an appropriate antibody. Alternatively they could be covalently bound to some other moiety to which an antibody fragment could attach.

Another possible type of therapeutic agent is a non-enzymic catalyst. This could be a transition metal attached to ligand(s). For instance Borggaard, Farver and Andersen, Acta Chem. Scand. 25 [1971] 3541 have shown that iron with ethylene diamine tetraacetic acid (EDTA) as ligand will catalyse the conversion of hydrogen peroxide to hydroxyl ion and an OH free radical which would be very short lived but also very toxic.

When there is more than one therapeutic agent it is particularly envisaged that these will be enzymes able to co-operate with each other. Of special interest is the combination of an oxidase such as glucose or galactose oxidase and a peroxidase such as horseradish peroxidase which uses peroxide to convert halide ions to oxidised halide species that are even more toxic than peroxide. A peroxidase may also use peroxide to convert thiocyanate to hypothiocyanate. It is also possible that a therapeutic agent will comprise two enzymes attached to a common intermediary. This may be a synthetic polymer having chemical functionality to enable the attachment of enzymes by chemical reaction. A suitable polymer is polyethyleneimine which is a branched polymer with amino groups at the ends of the branches.

Glucose oxidase and horseradish peroxidase are both enzymes with pendant glycosyl chains. Such enzymes can be covalently bound to polyethyleneimine by first oxidising the enzymes in aqueous solution with periodate to generate aldehyde groups in the pendant glycosyl chains. These groups will then form Schiff bases with amino groups on the polyethyleneimine, at alkaline pH (e.g. pH 9.5) after which reduction with borohydride can be used to reduce any unreacted aldehyde groups and also the Schiff bases. The latter increases stability of the link between enzyme and polymer.

The antibody fragments(s) and possibly the therapeutic agent(s) are incorporated in one or more pharmaceutically acceptable vehicles.

The therapeutic agent(s) may be included in the vehicle or one of the vehicles, but if the therapeutic agent is not covalently bound to the additional peptide of the first antibody, the therapeutic agent may be a material which is present in vivo in the general vicinity of the target site. The binding in accordance with the invention would then serve to concentrate the therapeutic agent onto the target site, thereby enhancing its activity against the target.

Where there are a plurality of antibody fragments which can combine spontaneously, it may be desirable to distribute them between a plurality of vehicles. The same applies when there is an antibody fragment able to bind to the therapeutic agent, and such agent itself. However, such precautions may not be necessary. An advantage of antibody fragments is that the complexes which form by antigen-antibody binding are fairly small and more stable than complexes with whole antibodies.

A product comprising a vehicle or vehicles containing therapeutic agent and antibodies could take a number of forms. If the target site is in the mouth, possibilities are mouthwash, toothpaste and a lozenge which will dissolve in the mouth. These forms of product could be used even when a plurality of vehicles are needed. For instance the product could be a two-component mouthwash which the user mixes immediately before use.

It could be a toothpaste having two components stored in the toothpaste container in such a way that they are kept separate or at least do not mix but are dispensed together and mix in the mouth of the user. Such two-component toothpaste products are known per se.

Another possible form of product providing a plurality of vehicles would be a lozenge to be sucked in the mouth, with the various components of the complex contained in separate regions of the lozenge. Three separate regions would preferably be used, and arranged so that the components of the complex were released in order, starting with the first (anti-target) antibodies. This would allow the complex to assemble on the target site.

Two vehicle forms could be used in combination as a way to provide a plurality of vehicles, e.g. toothpaste whose use is followed by a mouthwash or a lozenge.

When the therapeutic agent is an enzyme, the product may include a substrate for enzyme action, or it may rely on the enzyme substrate being present at the target site. Thus where the enzyme is glucose oxidase, directed at a target site in the mouth, the product could rely on dietary glucose as the enzyme substrate or it could itself incorporate glucose provided this was kept separate from the glucose oxidase.

If two enzymes are employed, the product may include substrates for both of them e.g. both glucose and a halide. Alternatively, only one substrate, or none at all may be included and reliance placed on substrate which comes from another source and happens to be present at the target site.

BRIEF DESCRIPTION OF DRAWING

A preferred embodiment of the invention is illustrated by the attached diagram which shows the complex formed on a target site.

DESCRIPTION OF PREFERRED EMBODIMENT

For attaching to the antigenic site 12 on the target 10 there is an Fv antibody fragment 14 with an additional peptide 16, which is several repeats of a shorter peptide 17, appended to the distal (C-terminal) end of one of the two peptide chains in the Fv fragment, so as to prolong that chain.

The therapeutic agents are glucose oxidase (G.Ox) and horseradish peroxidase (HRP). Each is bound by a respective Fv fragment 18,20 with specificity for the enzyme concerned, and with a single repeat of the peptide 17 appended to one peptide chain of the Fv fragment.

The peptides 17 appended to the anti-enzyme Fv fragments 18,20 become linked to portions 17 of the peptide 16 on the anti-target Fv fragment 14 by means of $F(ab)_2$ fragments 22 which bind specifically to these peptides 17. Since the $F(ab)_2$ fragments 22 are divalent they can form a bridge attaching an anti-enzyme fragment, with attached enzyme, to the anti-target fragment 14.

We claim:

1. A product for treating a human body target site, which site is located in the human mouth and is accessible by topical application, with a therapeutic agent, said product being selected from the group consisting of mouthwash, toothpaste, and lozenge, said product comprising:

(a) a therapeutic agent;

(b) a first antibody formed from at least one peptide chain and which is able to bind to the target site through antibody-antigen binding, said first antibody fragment having a first additional peptide other than a fragment of the same antibody, appended thereto through a covalent peptide bond; and (c) a second antibody fragment able to bind through antibody-antigen binding to said first additional peptide and to bind the therapeutic agent to said first additional peptide, whereby in use of the product binding of the first antibody fragment to the target site holds the therapeutic agent on the target site, for the therapeutic agent to act on the target site.

2. A product according to claim 1 which further comprises a third antibody fragment which is able to bind to the therapeutic agent through antibody-antigen binding and which has a second additional peptide appended to it through a covalent peptide bond, said second antibody fragment having two binding sites and being able to bind through antibody-antigen binding at one said binding site to said second additional peptide appended to said third antibody fragment and through antibody-antigen binding at the other of said two binding sites to said first additional peptide appended to said first antibody fragment.

3. A product according to claim 1 wherein the therapeutic agent is an enzyme.

4. A product according to claim 3 wherein the enzyme is an oxidase.

5. A product according to claim 1 wherein the first antibody fragment able to bind to the target site is a fragment of an antibody to an antigenic component of the bacteria in dental plaque.

6. A product according to claim 1 wherein the first antibody fragment able to bind to the target site is a fragment of an antibody to an organism selected from the group consisting of *S. mutans, S. sanguis, A. viscosus* and *A. naeslundii*.

7. A method of delivering a therapeutic agent to a target site comprising applying a product according to claim 1 to the locality of the target site.

8. A method of delivering a therapeutic agent to a human body target site which site is located in the human mouth and is accessible by topical application which method comprises applying a product comprising (a) a therapeutic agent;

(b) a first antibody fragment formed from at least one peptide chain and having a first additional peptide other than a fragment of the same antibody appended thereto by a covalent peptide bond so that the peptide chain of the antibody fragment is prolonged and terminated by said first additional peptide, and (c) a second antibody fragment able to bind through antibody-antigen binding to said first additional peptide, said second antibody fragment serving to link the therapeutic agent to said first additional peptide whereby the binding of the first antibody fragment to the target site holds the therapeutic agent on the target site, for the therapeutic agent to act on the target site.

9. A product for treating a human body target site, which site is located in the human mouth and is accessible by topical application, with a therapeutic agent, the product being selected from the group consisting of mouthwash, toothpaste, and lozenge, said product comprising:

(a) a therapeutic agent:

(b) a first antibody fragment formed from at least one peptide chain and which is able to bind to the target site, said antibody having at least a first additional peptide other than a fragment of the same antibody appended thereto through a covalent peptide bond so that the peptide chain of said first antibody fragment is prolonged and terminated by said first additional peptide, and (c) a second antibody fragment able to bind to said additional peptide and to said therapeutic agent.

10. A product according to claim 14 wherein said first additional peptide comprises a plurality of repeats of a shorter peptide.

* * * * *